United States Patent
Gilja et al.

(10) Patent No.: US 8,792,976 B2
(45) Date of Patent: Jul. 29, 2014

(54) BRAIN MACHINE INTERFACE

(75) Inventors: Vikash Gilja, San Francisco, CA (US);
Paul Nuyujukian, Stanford, CA (US);
Cynthia A Chestek, Menlo Park, CA (US); John P Cunningham, Saratoga, CA (US); Byron M. Yu, San Jose, CA (US); Stephen I Ryu, Menlo Park, CA (US); Krishna V. Shenoy, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 208 days.

(21) Appl. No.: 12/932,070

(22) Filed: Feb. 17, 2011

(65) Prior Publication Data

US 2011/0224572 A1 Sep. 15, 2011

Related U.S. Application Data

(60) Provisional application No. 61/338,460, filed on Feb. 18, 2010.

(51) Int. Cl.
*A61B 5/04* (2006.01)
*A61F 4/00* (2006.01)
*A61F 2/72* (2006.01)
*G06F 3/01* (2006.01)
*A61B 5/0476* (2006.01)
*A61F 2/70* (2006.01)

(52) U.S. Cl.
CPC ... *A61F 2/72* (2013.01); *A61F 4/00* (2013.01); *A61B 5/0476* (2013.01); *A61F 2002/704* (2013.01); *G06F 3/015* (2013.01)
USPC .......................... 600/545; 700/257; 700/263

(58) Field of Classification Search
USPC ......................... 600/372, 377, 378, 544, 545; 700/250–257, 262, 263
See application file for complete search history.

(56) References Cited

U.S. PATENT DOCUMENTS

2010/0274746 A1 * 10/2010 Rickert et al. .................. 706/14
2011/0060461 A1 * 3/2011 Velliste et al. ................ 700/254

* cited by examiner

*Primary Examiner* — Michael Kahelin
*Assistant Examiner* — Yunqing Wang
(74) *Attorney, Agent, or Firm* — Lumen Patent Firm

(57) ABSTRACT

Artificial control of a prosthetic device is provided. A brain machine interface contains a mapping of neural signals and corresponding intention estimating kinematics (e.g. positions and velocities) of a limb trajectory. The prosthetic device is controlled by the brain machine interface. During the control of the prosthetic device, a modified brain machine interface is developed by modifying the vectors of the velocities defined in the brain machine interface. The modified brain machine interface includes a new mapping of the neural signals and the intention estimating kinematics that can now be used to control the prosthetic device using recorded neural brain signals from a user of the prosthetic device. In one example, the intention estimating kinematics of the original and modified brain machine interface includes a Kalman filter modeling velocities as intentions and positions as feedback.

5 Claims, 6 Drawing Sheets

BRAIN MACHINE INTERFACE

CROSS-REFERENCE TO RELATED APPLICATIONS

This application claims priority from U.S. Provisional Patent Application 61/338,460 filed Feb. 18, 2010, which is incorporated herein by reference.

STATEMENT OF GOVERNMENT SPONSORED SUPPORT

This invention was made with Government support under contract N66001-06-C-8005 awarded by the Defense Advanced Research Projects Agency (DARPA) and under contracts NIH RO1-NS054283 and 1DP1OD006409 awarded by the National Institutes of Health (NIH). The US Government has certain rights in the invention.

FIELD OF THE INVENTION

The invention relates generally to neural prosthetics. In particular, the invention relates to brain machine interfaces.

BACKGROUND OF THE INVENTION

Brain-machine interfaces (BMIs) translate action potentials from cortical neurons into control signals for guiding prosthetic devices, such as computer cursors and robotic limbs, offering disabled patients greater interaction with the world. BMIs have recently demonstrated considerable promise in proof-of-concept laboratory animal experiments, as well as in human clinical trials. However, two critical barriers to successful translation remain. First, current BMIs move considerably slower and less accurately than the native arm. Second, they do not sustain performance across hours and days, or across behavioral tasks, without human intervention. The present invention addresses this need for increased performance and robustness and advances the art of neural prosthetics.

SUMMARY OF THE INVENTION

In one embodiment of the invention a method is provided for artificial control of a prosthetic device (e.g. a robotic limb, a computer cursor, or the like). A brain machine interface is stored on a computer-readable medium and executable by a computer. The brain machine interface contains a mapping from neural signals to corresponding intention estimating kinematics of a limb trajectory. The intention estimating kinematics includes positions and velocities. The neural signals are signals from cortical neurons related to volitional tasks.

The prosthetic device is controlled by the stored brain machine interface using recorded neural signals as input to said brain machine interface and the stored mapping of the brain machine interface to determine the intention estimating kinematics. The determined intention estimating kinematics then controls the prosthetic device and results in an executed movement of the prosthetic device.

During the control of the prosthetic device, a modified brain machine interface is developed by modifying (and storing by the computer) the vectors of the velocities defined in the brain machine interface. Each of the modifications of the velocity vectors includes changing the direction of the velocity vector towards an end target of the executed movement of the prosthetic device. Once on target, the velocity is set to zero. In one example, the velocity vectors are modified and stored at discrete intervals over the course of the executed movement of the prosthetic device.

The modified brain machine interface includes a new mapping of the neural signals and the intention estimating kinematics that can now be used to control the prosthetic device using recorded neural brain signals from a user of the prosthetic device. In one example, the intention estimating kinematics of the original and modified brain machine interface includes a Kalman filter modeling velocities as intentions and positions as feedback.

In another embodiment of the invention a neural prosthetic is provided having a prosthetic device and a controller. The controller is executable by a computer and interfaced with the prosthetic device. The controller has encoded (and stored on the computer) a mapping of neural signals and kinematics of the prosthetic device. Control kinematics is determined by the controller to control the prosthetic device based on neural signals received from a user of the prosthetic device. In one example of this device, the controller includes a Kalman filter which encodes the velocity kinematics as intentions and position kinematics as feedback.

DETAILED DESCRIPTION

Figure 1:
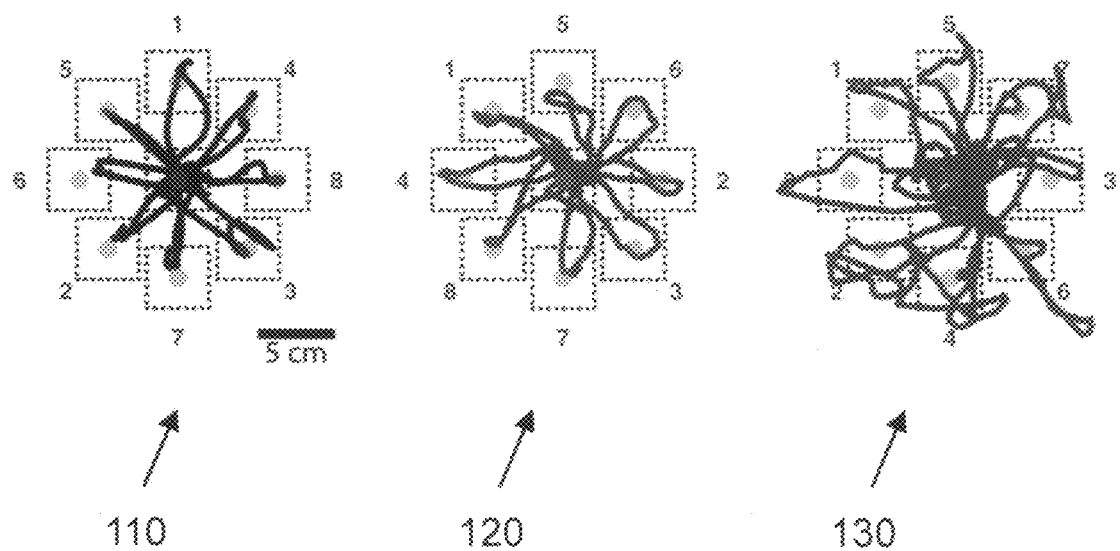
FIG. 1 shows according to an exemplary embodiment of the invention performance comparison between native arm control 110, the control algorithm according to examples of this invention 120, and a current state-of-the-art algorithm 130. Representative traces of cursor path during center-out-and-back reaches. The dashed lines are the target demand boxes for the eight peripheral targets and the central target is within the dashed boxes. Subsequent targets alternated between the center target and the peripheral target in the sequence indicated by the numbers shown. The traces shown are continuous for the duration of all sixteen center-out and return reaches.

In an example of the invention, monkeys were trained to acquire targets with a cursor controlled by either native arm movement or a neural control algorithm. FIG. 1 shows representative continuous, uninterrupted cursor movements for three different cursor-control modalities: native arm control 110, the control method according to an embodiment of the invention 120, and an example of a present state-of-the-art velocity Kalman filter (VKF, 130). Monkeys were required to move the computer cursor to a visual target (inside the dashed boxes) and hold the cursor at the target square for 500 ms to successfully complete a center-out-and-back reaching task and receive a liquid reward. Cursor movements with a controller according to an embodiment of the invention are straighter, faster, and stop better than those generated with the VKF (quantified data not shown). Furthermore, cursor movements produced using the controller according to an embodiment of the invention (120) are qualitatively similar to those produced by the native arm (110).

Figure 2:
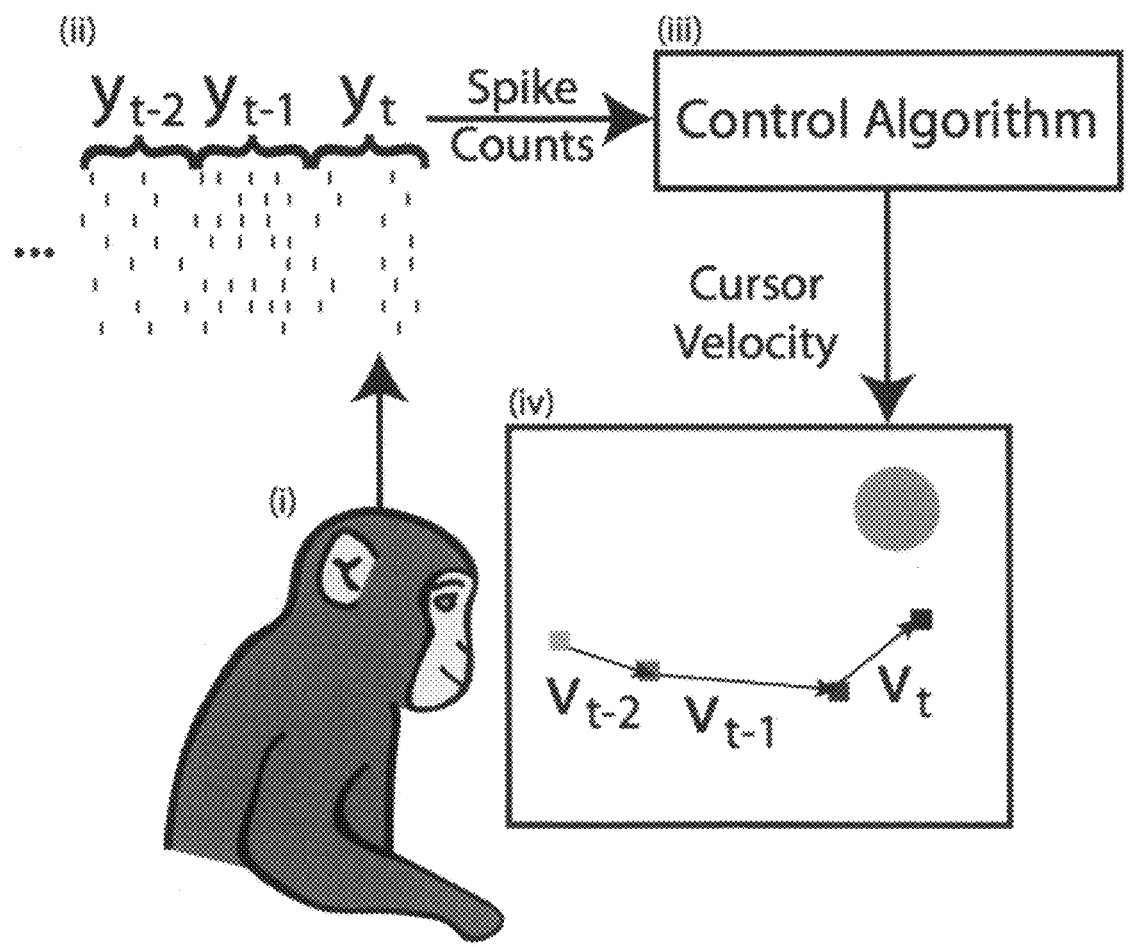
FIG. 2 shows according to an exemplary embodiment of the invention illustrations of an online neural control paradigm and control algorithm training methodology. The input to the neural control algorithm at time t is an array of spike counts, $y_t$, collected from implanted electrodes. The control algorithm translates the incoming neural data into a velocity output $v_t$.

This near native level of performance was achieved by a redefined control algorithm, as well as its training methodology, using a feedback control perspective. As shown in FIG. 2, when an animal is engaged in a brain machine interface (BMI) task the prosthetic device (e.g., computer cursor as shown, or a robotic arm) constitutes a new physical plant with dynamical properties that differ from those of the native arm. The subject controls this new plant by (i) modulating neural signals ($y_t$), which are then (ii) measured and (iii) decoded into a velocity by the control algorithm, which is (iv) used to update the cursor on the screen, affecting neural signals on subsequent time steps. Viewing the BMI from this feedback-control perspective leads to two new methods. The first method is a modification of BMI training method. The second method is an alteration to the design of the control algorithm. These are part of the control algorithm and produce the BMI results 120 in FIG. 1.

Figure 3:
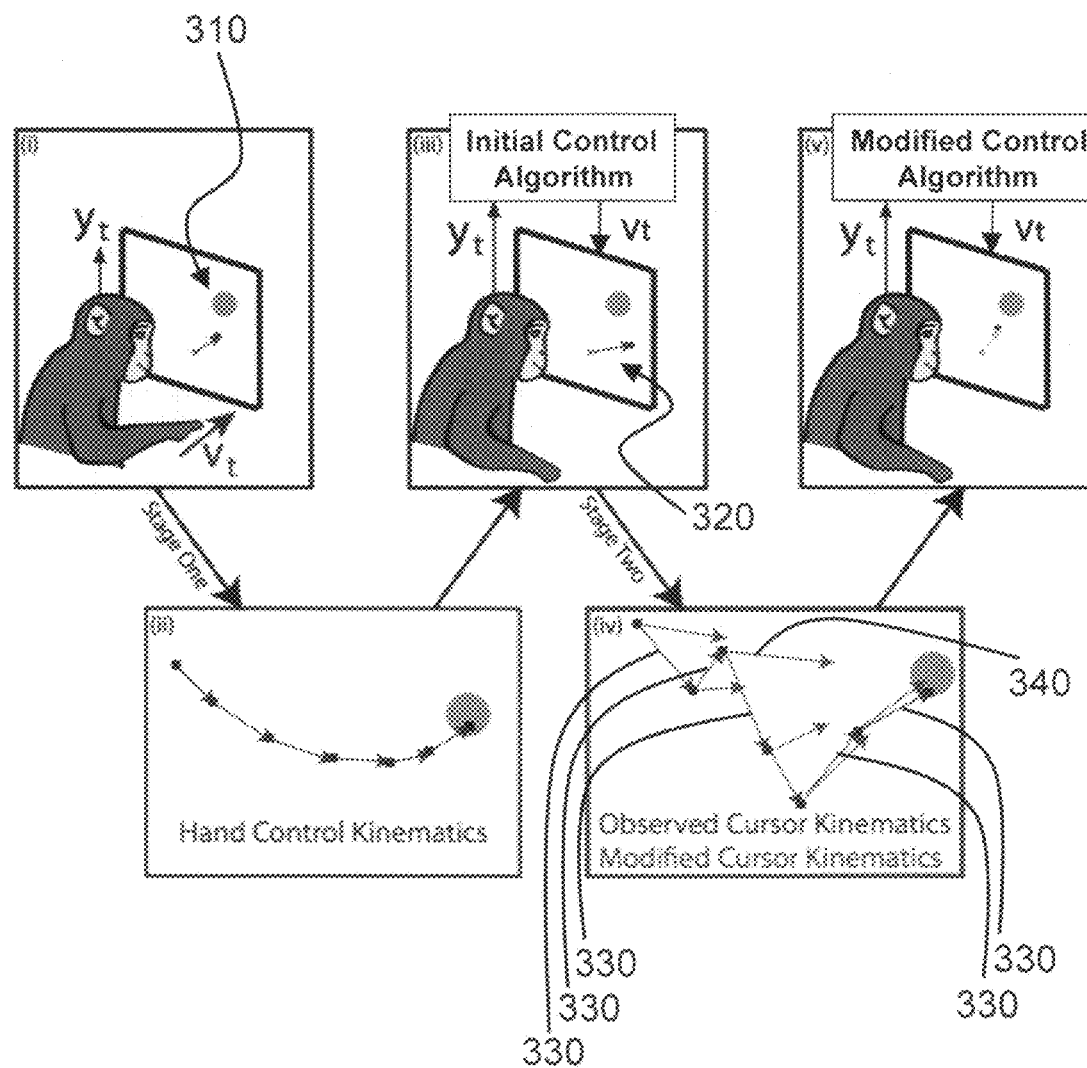
FIG. 3 shows according to an exemplary embodiment of the invention, the neural control algorithm two-stage training method. Initially, cursor kinematics and concurrent neural activity are collected during hand control (i). These kinematics (ii) are regressed against neural activity to generate an initial neural control algorithm. Then, a new set of cursor kinematics and neural activity are collected from closed loop control with the initial algorithm (iii). The cursor kinematics observed with this neural control algorithm (shown by arrrows 330 in (iv)) are the BMI algorithm estimates of the monkeys intended cursor velocity. We refine this estimate by rotating the velocities towards the goal (shown in arrows 340 in (iv)—note that only one arrow 340 is indicated for clarity purposes, however any other arrow that is not labeled 330 in iv is considered arrow 340). This set of modified cursor kinematics is regressed against neural activity to generate the modified BMI control algorithm, shown running in closed loop in (v).
Figure 4:
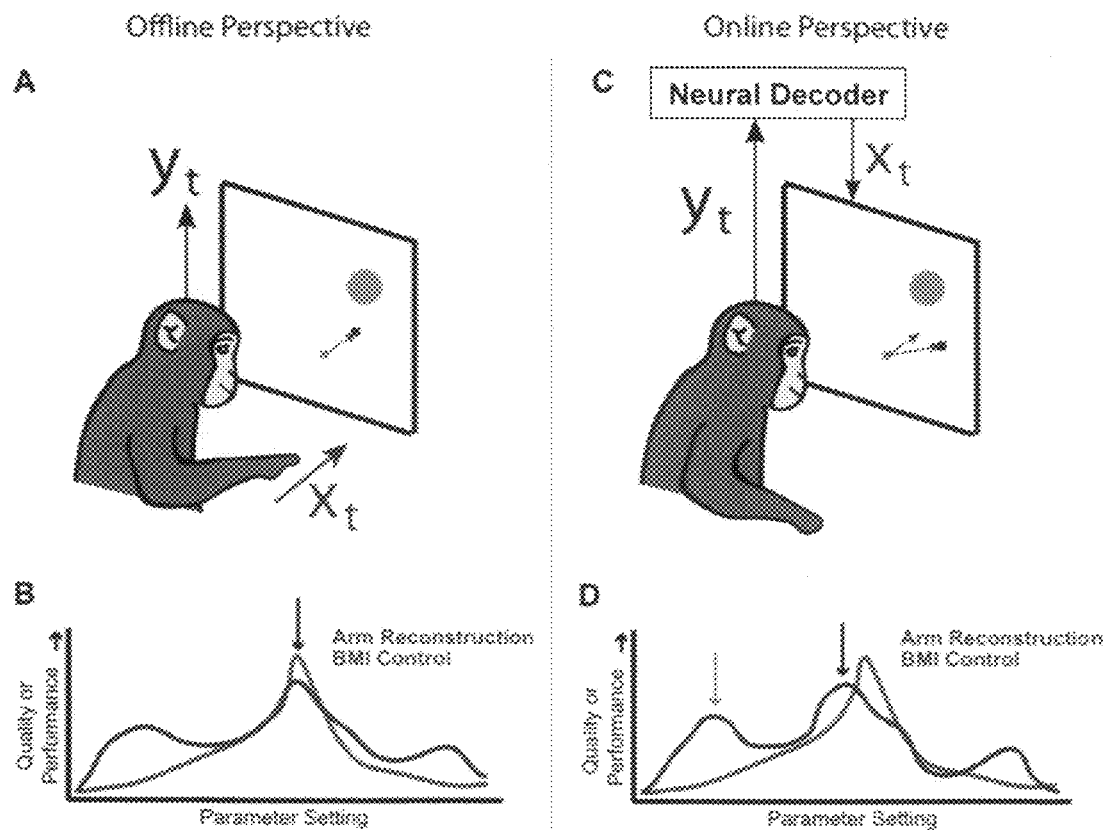
FIGS. 4A-D show according to an exemplary embodiment of the invention a comparison of the offline and online perspectives for neural prosthetic design: In (A) neural data $y_t$ and arm kinematics $x_t$ are collected to fit the parameters of a neural prosthetic. (B) is a hypothetical plot of parameter setting vs. quality/performance of the resulting system by such a fitting procedure, given the assumptions of the offline perspective, essentially that the maxima for arm reconstructions and BMI control occur with the same parameter settings. In (C) $x_t$ is no longer arm kinematics. Data are collected under closed loop neural control and $x_t$ is the kinematics of the neural cursor. This model fitting procedure assumes that ideal parameter settings for a neural prosthetic and arm reconstructions may vary, as indicated in hypothetical plot (D).
Figure 5:
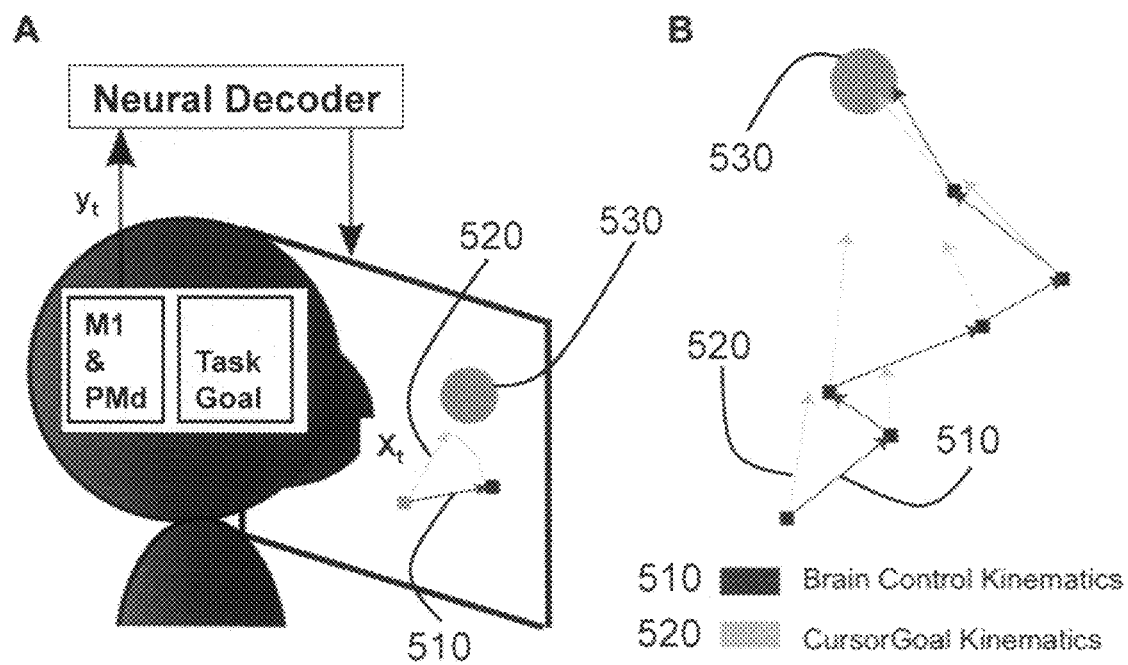
FIGS. 5A-B show according to an exemplary embodiment of the invention methods steps of collecting an "intention-based" kinematic training set: In (A) the user is engaged in online control with a neural cursor. During each moment in the session, the neural decoder drives the cursor with a velocity (vector 510). We assume that the user intended the cursor to generate a velocity towards target 530 in that moment, so we rotate this vector to generate an estimate of intended velocity (vector 520). This new set of kinematics is the modified cursor kinematics training set. (B) is an example of this transformation applied to successive cursor updates.

Previously reported control algorithms incorporate a mathematical model built to reconstruct native arm movement kinematics, implicitly assuming that neural control of the arm and prosthetic device are equivalent. However, embodiments of this invention take a different approach and incorporate the fact that the subject's control strategy may actually vary when asked to operate different plants with different dynamics. FIG. 3 outlines the two-stage BMI optimization procedure according to exemplary embodiments of the invention. In the first stage, the monkey controls the cursor using his arm (i in FIG. 3). An initial model is fit using arm trajectories and simultaneously recorded neural signals (ii in FIG. 3). The monkey then controls the cursor using the BMI with this initial model (iii in FIG. 3). This model's cursor trajectories are then refined by incorporating knowledge of the monkey's intention (iv in FIG. 3), leading to a final model (modified BMI) that is used for the remainder of the experiment (v in FIG. 3).

The first method according to an embodiment of the invention is to fit the BMI against a novel set of kinematics. Ideally, instead of fitting neural activity against the kinematics of native arm movements, we fit to the monkey's intended cursor kinematics during closed loop neural control. Since one would lack explicit access to the monkey's intentions, we make the assumption that the monkey always wishes to move towards the target 310, as this is how the native arm moves and is also the best strategy for rapidly acquiring rewards. We employ this assumption to estimate the monkey's intention from cursor movements collected during the initial control session (iii in FIG. 3). Specifically, as shown by iv in FIG. 3, the original BMI cursor movement velocity vectors (320) are rotated towards the target (310). When the cursor is on target, we assume an intention of zero velocity. These modified cursor kinematics and the corresponding neural data are used to fit the modified BMI, thereby arriving at the final control algorithm.

It is important to note that this transformation is applied only to the training data: during online control the BMI has no prior knowledge of the subjects task or goal, or the placement of the targets in the workspace. On subsequent BMI sessions, step-one (arm control) can be skipped (i.e. ii in FIG. 3), and the monkey can begin at step-two (initial BMI control) in FIG. 3) with model parameters from for example a previous day. Although the initial quality of BMI cursor control (arrows 330 in iv in FIG. 3) is often lower on the second day when starting directly with step-two, performance is restored when the model is optimized with the modified cursor kinematics (340, iv in FIG. 3—only one arrow 340 is indicated for clarity purposes, however any other arrow that is not labeled 330 is considered arrow 340). This approach was employed for up to five consecutive days, and performance is on par with that shown in FIG. 1 (110, 120).

The second method attempts to capture the observation that neural activity is correlated with not only the velocity of the cursor but also its position. Most existing BMIs model a relationship between neural firing and either velocity or position. Human clinical trials have shown that BMIs modeling velocity have higher performance. However, if the control algorithm only models the velocity relationship, then a position based increase in firing will result in an increase or decrease in cursor velocity, which is an undesired effect. To mitigate this effect, in one embodiment of this invention, we explicitly model velocity as the users intention, and model position as a signal that is fed back as the user controls the cursor and sees its behavior. This feedback-modified Kalman filter allows the user to control the velocity of the cursor with the measured neural signals while taking into account that this signal is influenced (or corrupted) by the current position of the cursor. Since the BMI knows the position of the cursor it is not estimated from the measured neural signals. Instead, the expected contribution of position to neural activity is removed. This results in a less position-dependent neural data stream, which in turn enables more accurate estimation of the intended cursor velocity as evidenced by higher performance (120 in FIG. 1).

Long-duration, continuous, high-performance operation is central to the successful translation of BMIs to human patients. To this end, and in further embodiments of this invention, we made three specific design choices for the BMI, in addition to the two methods described supra. First, we did not employ spike sorting, the process of classifying each spike based on the shape of its action potential. The goal of this classification is to separate single channels composed of spikes from many neurons into multiple channels to access the spiking activity of individual neurons. This is a standard practice in neuroscience and also in BMI-design, and can yield the highest information per electrode, but it adds the challenge of tracking each sorted action potential due to changes in amplitude over time. To avoid these signal instabilities, instead of spike sorting, we counted the number of threshold crossings per electrode within a time window. Second, while most BMI designs admit neural data from one or more neural integration time windows (e.g., 100 ms time bin; multiple 50 ms time bins in linear filter with history as far back as 1 sec) we elected to use a single time bin of 50 ms. This was determined through a series of experiments with humans using an online prosthetic simulator (OPS), indicating that shorter time bins are preferable due to their lower latency and therefore reduced closed-loop feedback time. Control experiments with our monkeys performing BMI tasks are consistent with these OPS results. Finally, the number of highly distinguishable single neurons on an electrode array tends to decrease over time, however multiunit activity can often have BMI relevant tuning. The results shown in FIG. 1 were acquired from arrays several months to years post implantation. By employing these somewhat older arrays, which had relatively few clearly distinguishable single units, we were able to confirm that threshold-crossing based multi-unit activity together with the control algorithm according to embodiments described herein is able to provide high performance for months and years post array implantation.

These levels of sustained performance and robustness demonstrate the potential to provide functional restoration for patients with a limited ability to move and act upon the world. For patients suffering from neurological injury and disease, although descending pathways are compromised, motor cortex may be intact, permitting the use of this class of technology. In recent years, a number of brain interface technologies using a variety of signal sources, such as the intra-cortical technology described here, electroencephalography (EEG), and electrocorticography (ECoG), have been developed. The BMI community continues to create options for disabled individuals and assess relative risk and benefit. The performance and robustness advances demonstrated herein, as well as the system design methodology, should help increase the clinical viability of intra-cortical based BMIs.

Experimental Methods

In an exemplary embodiment, experiments were conducted with adult male rhesus macaques, implanted with 96 electrode Utah arrays (Blackrock Microsystems Inc., Salt Lake City, Utah) using standard neurosurgical techniques. Monkeys were implanted e.g. 19-27 months or 4-8 months prior to the study. Electrode arrays were implanted in a region spanning the arm representation of the dorsal aspect of pre-motor cortex (PMd) and primary motor cortex (M1), as estimated visually from local anatomical landmarks.

The macaques were trained to make point-to-point reaches in a 2D plane with a virtual cursor controlled by movements of the contralateral arm or by the output of a neural decoder. The virtual cursor and targets were presented in an immersive 3D environment. Hand position data were measured with an infrared reflective bead tracking system. Spike counts used in all studies were collected by applying a single negative threshold, set to 4.5× root mean square of the spike band of each neural channel—no spike sorting was used. Behavioral control and decoding were run on separate PCs with custom code running on the PC platform, communication latencies between these two systems was 3 ms. This system enabled millisecond timing precision in all computations. Neural data was initially processed by a recording system and was available to the behavioral control system within 5±1 ms. Visual presentation was provided via two LCD monitors with refresh rates at 120 Hz, yielding frame updates within 11±3 ms. The monitors were used to form a Wheatstone stereograph using two mirrors to fuse the two displays into a single stereo percept.

Kalman Filter

Many control algorithms, or continuous decoding methods, have been studied for neural prosthetics applications such as the Kalman filter. The basic intended application of the Kalman filter is to track the state of a dynamical system throughout time using noisy measurements. Although we have a model of how dynamics evolve through time, the underlying system may not be deterministic. If we know the state of the system perfectly at time t, our dynamical model only gives us an estimate of the system state at time t+1. We can use the measurements (or observations) of the system to refine our estimate, and the Kalman filter provides the method by which these sources of information are fused over time. The filter can be presented from a dynamical Bayesian network (DBN) perspective, and is considered to be one of the simplest DBNs.

Figure 6:
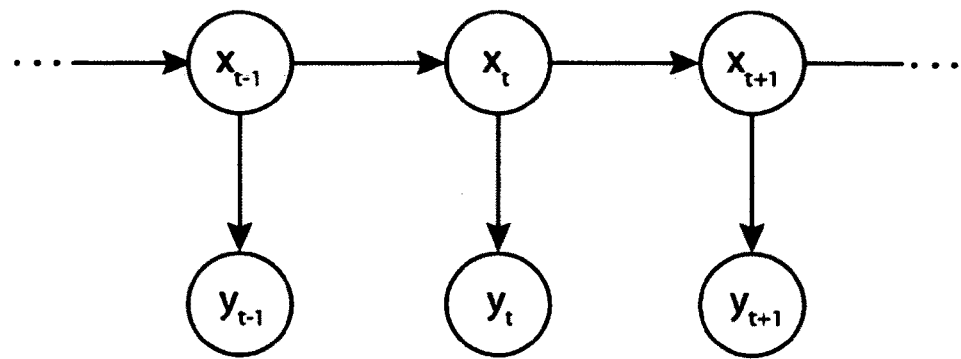
FIG. 6 shows according to an exemplary embodiment of the invention a graphical model representing the assumptions of a Kalman filter. $x_t$ and $y_t$ are the system state and measurement at time t, respectively.
Figure 7:
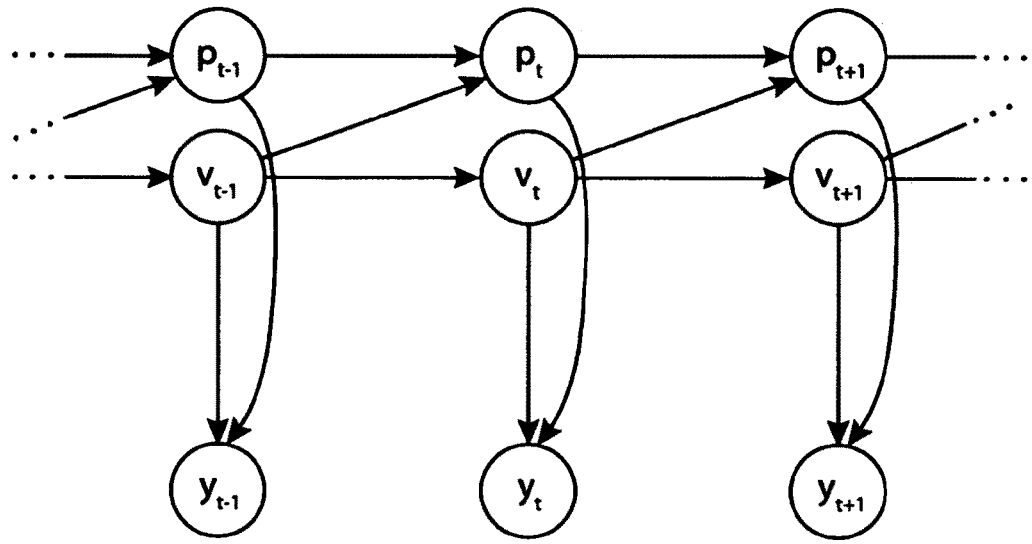
FIG. 7 shows according to an exemplary embodiment of the invention a graphical representation of the position/velocity Kalman filter used for neural control.

A graphical model of the basic DBN representation of the Kalman filter is shown in FIG. 6. For neural prosthetic applications, the system state vector $x_t$ is commonly used to represent the kinematic state. In embodiments of this invention, the state vector represents position and velocity of the cursor:

$$(x_t = [pos_t^{vert}, pos_t^{horiz}, vel_t^{vert}, vel_t^{horiz}, 1]^T)$$

The constant 1 is added to the vector to allow observations to have a fixed offset (i.e., baseline firing rate). $y_t$ is the measured neural signal, which is binned spike counts. The choice of bin width can affect the quality of prosthetic control: assuming local stationarity, long bin widths can provide a more accurate picture of neural state but with poorer time resolution. Thus, there is an implicit tradeoff between how quickly the prosthetic can change state and how accurately those states are estimated. Typical bin widths used in studies range from 10 ms to 300 ms. Through online study, we find that shorter bin widths result in better performance. The results discussed in this study use 25 or 50 ms bin widths.

When applying the standard Kalman filter, the system is modeled with linear dynamics, a linear relationship between kinematic state and neural observations, and Gaussian distributed noise and uncertainty:

$$x_t = Ax_{t-1} + W_t \quad (1)$$

$$y_t = Cx_t + q_t \quad (2)$$

where $A \in R^{p \times p}$ and $C \in R^{k \times p}$ represent the state and observation matrices, and w and q are additive, Gaussian noise sources, defined as $w_t \sim \mathcal{N}(0, W)$ and $q_t \sim \mathcal{N}(0, Q)$. A is the linear transformation from previous kinematic state, or dynamics, and C is mapping from kinematic state to expected observation. This formulation allows for very fast inference (decoding) of kinematics from neural activity and the parameters $\theta = \{A, C, W, Q\}$ can be quickly learned from training data. The observation model of the Kalman filter, C and Q, is fit by regressing neural activity on observed arm kinematics:

$$C = YX^T(XX^T)^{-1} \tag{3}$$

$$Q = \frac{1}{D}(Y - CX)(Y - CX)^T \tag{4}$$

where X and Y are the matrices formed by tiling the D total data points $x_t$ and $y_t$. For the Kalman filter, we also assume that the dynamics of observed arm kinematics match the desired neural cursor kinematics, and so the parameters of the dynamics or trajectory model, A and W, are fit from observed arm kinematics:

$$A = X_2 X_1^T (X_1 X_1^T)^{-1} \tag{5}$$

$$W = \frac{1}{D-1}(X_2 - AX_1)(X_2 - AX_1)^T \tag{6}$$

$X_1$ is all columns of X except for the last column and $X_2$ is all columns of X except for the first column, introducing a one time-step shift between the two matrices.

In practice we constrain the form of the A and W matrices to obey simple physical kinematics, integrated velocity perfectly explains position:

$$A = \begin{pmatrix} 1 & 0 & dt & 0 & 0 \\ 0 & 1 & 0 & dt & 0 \\ 0 & 0 & a_{vel_{horiz},vel_{horiz}} & a_{vel_{horiz},vel_{vert}} & 0 \\ 0 & 0 & a_{vel_{vert},vel_{horiz}} & a_{vel_{vert},vel_{vert}} & 0 \\ 0 & 0 & 0 & 0 & 1 \end{pmatrix} \tag{7}$$

After fitting with either set of kinematics, $a_{vel_{vert},vel_{horiz}}$ and $a_{vel_{horiz},vel_{vert}}$ are typically close to 0 and $a_{vel_{horiz},vel_{horiz}}$, $a_{vel_{vert},vel_{vert}}$ are less than 1. The resulting model introduces damped velocity dynamics. Therefore, given no neural measurements, we expect a cursor in motion to smoothly slow down. We also constrain the W matrix, so that for the dynamics model, integrated velocity fully explains position:

$$W = \begin{pmatrix} 0 & 0 & 0 & 0 & 0 \\ 0 & 0 & 0 & 0 & 0 \\ 0 & 0 & w_{vel_{horiz},vel_{horiz}} & w_{vel_{horiz},vel_{vert}} & 0 \\ 0 & 0 & w_{vel_{vert},vel_{horiz}} & w_{vel_{vert},vel_{vert}} & 0 \\ 0 & 0 & 0 & 0 & 0 \end{pmatrix} \tag{8}$$

If we fit the full C matrix, the resulting filter is a position/velocity Kalman filter (neural firing simultaneously describes position and velocity). If we constrain the position terms to be 0, the resulting filter is a velocity only Kalman filter (neural firing describes only velocity).

Kalman Filter Design

Imagine a hypothetical prosthetic that decodes from a single neuron. This neuron fires more vigorously when leftward velocities are instructed and also happens to fire more when the cursor is positioned on the left side of the workspace. If our decoder translates this firing rate into velocities, without any knowledge of positional effects, every time the cursor enters the left side of the screen positive feedback will accelerate the cursor to the left. Positive feedback results because the firing rate increase due to leftward position is mapped to leftward velocity by the decoder, thereby driving the cursor faster to the left than the user intends. By accounting for position, some of the increased firing can be explained by the position of the cursor, and this feedback effect can be mitigated.

However, the way in which the position/velocity Kalman filter models the relationship between position and velocity leads to undesired high frequency jitter in the cursor position. The dynamics model described in the Kalman filter section supra is physically based, acting like an object moving in a gravity free 2-D space with damped velocity, so we may expect cursor position to evolve smoothly. However, the Kalman filter translates velocity uncertainty into position uncertainty at subsequent time-steps. To understand why this occurs, we examine how the filter is run online. At time t we have a previous estimate of the kinematic state, $\hat{x}_{t-1}$ and a new neural observation, $y_t$. The first step in each filter iteration is to apply the dynamics model, estimating $x_t = [p_t, v_t]$ with all neural observations up to time t−1. This is the a priori estimate of $x_t$:

$$\hat{x}_{t|t-1} = A\hat{x}_{t-1} \tag{9}$$

The model also estimates the a priori covariance (or uncertainty) of $\hat{x}_{t|t-1}$:

$$P_{t|t-1} = AP_{t-1}A^T + W \tag{10}$$

We know that the W adds no uncertainty to a priori position, given its structure as defined in Equation 8. However, $AP_{t-1}A^T$ translates previous velocity uncertainty into current position uncertainty. This makes sense: if we do not know the previous velocity with certainty, we do not know the integrated velocity with certainty and so our position estimate may have error. Thus, in practice, there is uncertainty in the a priori estimate of every kinematic variable. To see how this uncertainty in position translates to jitter in the decode, we can continue to step through the algorithm. Once we update the a priori estimate, we must incorporate the information acquired from the neural observation. The model has an expected neural output given $\hat{x}_{t|t-1}$, and this output may not match $y_t$. This error is the measurement residual, $\tilde{y}_t$, and also has a corresponding covariance (or uncertainty) estimate, $S_t$:

$$\tilde{y}_t = y_t - C\hat{x}_{t|t-1} \tag{11}$$

$$S_t = CP_{t|t-1}C^T + Q \tag{12}$$

If this residual is nonzero (which is almost always true in practice), then the measurement and $\hat{x}_{t|t-1}$ do not agree and we must decide how much weight this observation residual has relative to $\hat{x}_{t|t-1}$. This weight is based on how much uncertainty is present in the kinematics suggested by the a priori estimate of $x_t$ versus the kinematics suggested by $\tilde{y}_t$:

$$K_t = P_{t|t-1}C^T S_t^{-1} \tag{13}$$

Finally, we can use $K_t$, called the Kalman gain, to find the estimate of x, that incorporates all of the neural observations up to time t, this is called the a posteriori estimate. We calculate the a posteriori estimate for $x_t$ and its covariance:

$$\hat{x}_t = \hat{x}_{t|t-1} + K_t \tilde{y}_t \quad (14)$$

$$P_t = (I - K_t C) P_{t|t-1} \quad (15)$$

The Kalman gain transforms the measurement residual into the kinematic space. Since a priori estimates of both position and velocity kinematics have uncertainty and neural measurements have information about position and velocity, the Kalman gain will translate neural measurements into updated a posteriori estimates of both position and velocity. For offline trajectory reconstruction, this makes sense, as this coupled position/velocity uncertainty exists throughout time. However, these assumptions breakdown in the online setting, and substantially limit performance.

We must distinguish online and offline use of the Kalman filter. In the online setting, the user is presented with the a posteriori estimate of cursor kinematics at every time-step. If we believe that the user sees and internalizes the presentation of the cursor on the screen at each time-step, then the way in which we model a posteriori covariance no longer makes sense, as the user accepts the presented position as the current position state. By presenting the decode to the user, we are creating a causal intervention, that explicitly sets the value of the kinematic variable. This operation is defined by probability theory and is well described by the causal calculus.

Figure 8:
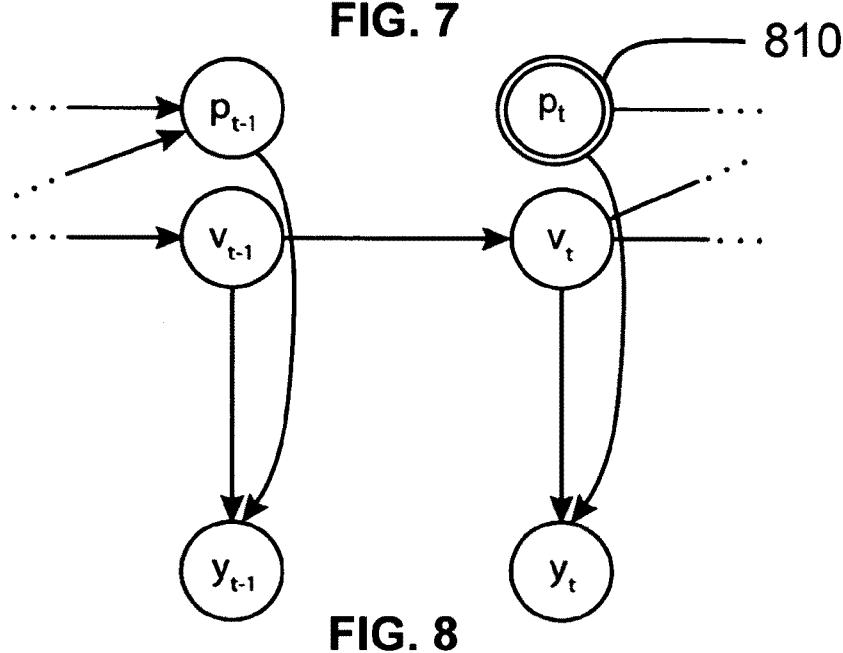
FIG. 8 shows according to an exemplary embodiment of the invention a position/velocity Kalman filter modeling position feedback through causal intervention. In other words, the Kalman filter models velocities as intentions and positions as feedback.

As a first step to modify the filter to incorporate this feedback, we presume that the user internalizes the filter's estimate of cursor position, $\hat{p}_{t-1}$, with complete certainty by time t. Accordingly, $p_t$ is explicitly set to $A_p \hat{p}_{t-1}$, where $A_p$ is the upper-left block of the state matrix A. In other words, since the user knows the previous cursor position $\hat{p}_{t-1}$ via feedback, this forward model is exact at $p_t = A_p \hat{p}_{t-1}$. This is shown graphically in FIG. 8, where the intervened variable is shown by 810 (adding another circle is standard notation for causal interventions). Note also that the arrows coming into $p_t$ have been removed, to indicate that $p_t$ has been externally set and uncertainty is not propagated.

The result of this intervention is to remove uncertainty in $p_t$. All parameter fitting methods described in previous sections remain unchanged. To implement this position feedback filter, only a small change in the online operation of the standard filter is necessary. All steps outlined above are the same except for Equation 10. Previously, we had:

$$P_{t|t-1} = A P_t A^T + W \quad (16)$$

$$\text{where } P_{t|t-1} = \begin{bmatrix} P_{p,p} & P_{p,v} \\ P_{v,p} & P_{v,v} \end{bmatrix}$$

where each block of the matrix $P_{t|t-1}$ represents the uncertainty propagated from previous kinematic estimates (position to position, position to velocity, and so on). Since we have intervened and set $p_t$ with feedback, this matrix becomes:

$$\overline{P}_{t|t-1} = \begin{bmatrix} 0 & 0 \\ 0 & P_{v,v} \end{bmatrix}. \quad (17)$$

Otherwise, this filter is run in the same manner as the standard Kalman filter.

What is claimed is:

1. A method for artificial control of a prosthetic device, comprising:
   a) storing a brain machine interface on a computer-readable medium and executable by a computer, wherein said brain machine interface comprises a mapping from neural signals to corresponding intention estimating kinematics of a limb trajectory, wherein said intention estimating kinematics comprises positions and velocities;
   b) controlling said prosthetic device by said stored brain machine interface using recorded neural signals as input to said brain machine interface and said mapping of said brain machine interface to determine the intention estimating kinematics to control said prosthetic device, wherein said controlling results in an executed movement of said prosthetic device;
   c) developing a modified brain machine interface by modifying and storing by said computer during said control of said prosthetic device, at discrete time intervals over the course of said executed movement of said prosthetic device, the vectors of said velocities in terms of direction as well as amplitude defined in said brain machine interface, wherein each of said modifications of said velocity vectors comprises changing the direction of said velocity vector towards an end target of said executed movement of said prosthetic device;
   d) using said modified brain machine interface to control said prosthetic device; and
   e) applying a kinematics feedback filter in both said brain machine interface and said modified brain machine interface, wherein said kinematics feedback filter applies a covariance matrix of an a posteriori estimate of said intention estimating kinematics at each time step of said discrete time intervals, whereby said positions are modeled as feedback from said interfaces to a user of said prosthetic device and said velocities are modeled as intentions of said user of said prosthetic device.

2. The method as set forth in claim 1, wherein said modified brain machine interface comprises a new mapping of said neural signals and said intention estimating kinematics.

3. The method as set forth in claim 1, wherein said a posteriori estimates of said positions in said covariance matrix are set to zero.

4. The method as set forth in claim 1, wherein said prosthetic device is a robotic limb or a computer cursor.

5. The method as set forth in claim 1, wherein said neural signals are signals from cortical neurons related to volitional tasks.

* * * * *